(12) United States Patent
Naito

(10) Patent No.: US 11,642,548 B2
(45) Date of Patent: May 9, 2023

(54) STERILIZATION METHOD AND STERILIZATION APPARATUS

(71) Applicant: Ushio Denki Kabushiki Kaisha, Tokyo (JP)

(72) Inventor: Keisuke Naito, Tokyo (JP)

(73) Assignee: Ushio Denki Kabushiki Kaisha, Tokyo (JP)

( * ) Notice: Subject to any disclaimer, the term of this patent is extended or adjusted under 35 U.S.C. 154(b) by 133 days.

(21) Appl. No.: 17/396,513

(22) Filed: Aug. 6, 2021

(65) Prior Publication Data

US 2021/0361971 A1    Nov. 25, 2021

Related U.S. Application Data

(62) Division of application No. 16/651,847, filed as application No. PCT/JP2018/032827 on Sep. 5, 2018, now abandoned.

(30) Foreign Application Priority Data

Sep. 28, 2017  (JP) .............................. JP2017-188610

(51) Int. Cl.
*A61N 5/06* (2006.01)
*A61K 8/44* (2006.01)

(52) U.S. Cl.
CPC .............. *A61N 5/0624* (2013.01); *A61K 8/44* (2013.01); *A61N 5/0616* (2013.01); *A61K 2121/00* (2013.01); *A61N 2005/0661* (2013.01)

(58) Field of Classification Search
CPC ................ A61N 5/0624; A61N 5/0616; A61N 2005/0661; A61N 2005/0642; A61N 5/06–2005/073; A61K 8/44; A61K 2121/00; A61Q 17/04; A61L 2/00–2/28
See application file for complete search history.

(56) References Cited

U.S. PATENT DOCUMENTS 6,254,625 B1    7/2001  Rosenthal et al.
8,142,713 B2 *  3/2012  Gordon ..................... A61L 2/10
                                                    422/906

(Continued)

FOREIGN PATENT DOCUMENTS

CN    102525864 A    7/2012
EP    3 195 900 A1   7/2017

(Continued)

OTHER PUBLICATIONS

International Search Report issued in PCT/JP2018/032827; dated Dec. 11, 2018.

(Continued)

*Primary Examiner* — Jonathan T Kuo
(74) *Attorney, Agent, or Firm* — Studebaker & Brackett PC

(57) ABSTRACT

Provided a method of sterilization by ultraviolet irradiation whereby effects on the human body can be mitigated and an odor that arises after ultraviolet irradiation can be controlled. The sterilization method includes: a step (a) of irradiating a skin of a hand or arm with ultraviolet having a wavelength of 200 nm or more and 230 nm or less; and a step (b) of applying a topical skin preparation, cosmetic, or aqueous solution containing at least one amino acid or amino acid derivative selected from an amino acid group A to a region of the skin irradiated with the ultraviolet. The amino acid group A includes valine, leucine, isoleucine, glutamic acid, arginine, serine, aspartic acid, proline, and glycine.

4 Claims, 2 Drawing Sheets

(56) References Cited

U.S. PATENT DOCUMENTS

| | | | |
|---|---|---|---|
| 8,735,442 B2* | 5/2014 | Ashida | A61P 17/02 |
| | | | 514/428 |
| 9,050,383 B2 | 6/2015 | Gray | |
| 11,351,393 B2* | 6/2022 | Feldreich | A61N 5/0624 |
| 2002/0173833 A1 | 11/2002 | Korman et al. | |
| 2007/0256226 A1 | 11/2007 | Pinizzotto | |
| 2008/0199354 A1* | 8/2008 | Gordon | A61L 2/10 |
| | | | 422/186.3 |
| 2009/0143842 A1 | 6/2009 | Cumbie et al. | |
| 2010/0028201 A1 | 2/2010 | Neister | |
| 2011/0044848 A1 | 2/2011 | Wright | |
| 2011/0082525 A1 | 4/2011 | Bornstein | |
| 2012/0142941 A1* | 6/2012 | Ashida | A61P 17/16 |
| | | | 562/557 |
| 2013/0129567 A1 | 5/2013 | Gray | |
| 2015/0045720 A1 | 2/2015 | Kanno et al. | |
| 2016/0107000 A1 | 4/2016 | Randers-Pehrson et al. | |
| 2016/0114067 A1 | 4/2016 | Dobrinsky et al. | |
| 2017/0000917 A1 | 1/2017 | Stibich et al. | |
| 2018/0169279 A1 | 6/2018 | Randers-Pehrson et al. | |
| 2018/0243582 A1 | 8/2018 | Kaneda et al. | |
| 2019/0126057 A1* | 5/2019 | Feldreich | A61N 5/062 |

FOREIGN PATENT DOCUMENTS

| | | |
|---|---|---|
| JP | S61-79461 A | 4/1986 |
| JP | 3157460 U | 2/2010 |
| JP | 2014-508612 A | 4/2014 |
| JP | 2015-134790 A | 7/2015 |
| JP | 6025756 B2 | 11/2016 |
| JP | 2017-038671 A | 2/2017 |
| JP | 2017-168252 A | 9/2017 |
| KR | 10-1522849 B1 | 6/2015 |
| WO | 2012/122210 A1 | 9/2012 |
| WO | 2016/196904 A1 | 12/2016 |

OTHER PUBLICATIONS

Notice of Decision to Grant a Patent issued to JP Application No. 2017-188610, dated Feb. 6, 2019.

Notification of Transmittal of Translation of the International Preliminary Report on Patentability (Chapter I) and Translation of Written Opinion of the International Searching Authority; PCT/JP2018/032827; dated Apr. 9, 2020.

The extended European search report issued by the European Patent Office dated Jun. 22, 2020, which corresponds to European Patent Application No. 18860334.4-1122 and is related to U.S. Appl. No. 16/651,847.

An Office Action issued by the China National Intellectual Property Administration dated Sep. 1, 2020, which corresponds to Chinese Application No. 201880055329.4 and is related to U.S. Appl. No. 16/651,847 with English language translation.

Communication pursuant to Article 94(3) EPC issued by the European Patent Office dated Apr. 28, 2021, which corresponds to European Application No. 18860334.4-1122 and is related to U.S. Appl. No. 16/651,847.

* cited by examiner

STERILIZATION METHOD AND STERILIZATION APPARATUS

CROSS-REFERENCE TO RELATED APPLICATIONS

This application is a Divisional Application of U.S. patent application Ser. No. 16/651,847, filed on Mar. 27, 2020, which is the U.S. National Phase of International Application No. PCT/JP2018/032827, filed on Sep. 5, 2018, which claims priority to and the benefit of Japanese Patent Application No. 2017-188610, filed on Sep. 28, 2017, the entire contents of which are incorporated herein by reference.

TECHNICAL FIELD

The present invention relates to a sterilization method and a sterilization apparatus, and more particularly to a method and apparatus for sterilizing the skin of human hands or arms.

BACKGROUND ART

Ultraviolet irradiation sterilization techniques have been known before. As known, for example, the light-absorbing characteristics of DNA indicate that DNA has a peak absorption at around the wavelength of 260 nm. The radiation spectrum of a low-pressure mercury lamp shows a peak around the wavelength of 254 nm. Therefore, sterilization techniques with low-pressure mercury lamps are widely used.

It is known, however, that irradiation of the human body with this wavelength band of ultraviolet entails the risk of effects on the human body. The skin is composed of three parts, from superficial to deep, the epidermis, the dermis, and the subcutaneous tissue below. The epidermis has four layers, from superficial to deep, stratum corneum, stratum granulosum, stratum spinosum, and stratum basale. When the human body is irradiated with ultraviolet at a wavelength of 254 nm, the light passes through the stratum corneum and reaches the stratum granulosum or stratum spinosum, and sometimes even the stratum basale, and is absorbed by the DNA in the cells present in these layers. This results in a risk of skin cancer.

In view of such a problem, Patent Document 1 listed below discloses a sterilization technique that uses 207 nm-220 nm wavelength ultraviolet to avoid risks on the human body in clinical sites.

PRIOR ART DOCUMENT

Patent Document

Patent Document 1: Japanese Patent No. 6025756

SUMMARY OF THE INVENTION

Problems to be Solved by the Invention

Sterilization is essential in clinical sites because of the need to control secondary infections. The technique of Patent Document 1 mentioned above allows for ultraviolet irradiation without any protection means such as protective clothing, protective hood, and protective goggles, and provides the advantage that sterilization can be performed with reduced effects on the bodies of patients and hospital staff.

Sterilization is no less essential particularly in food-handling sites than in clinical sites. Commonly, alcohol sterilization is obligatory when handling food in food factories or convenience stores. In a food factory, for example, workers first wash their hands and arms with soap before an antiseptic wash with alcohol spray, before entering into a factory line area. Often, this operation is performed every time a worker enters a line area, or every time a worker changes assigned locations. In shops where food is handled, too, the store staff often perform the practice of the preliminary wash with soap and the antiseptic wash with alcohol spray each time they handle food.

However, such practice of washing the hands and arms with soap and alcohol several times a day entails the risk of skin problems due to the oil components of the skin being removed. Also, such frequent washing forces the staff to bear a heavy burden.

Based on an assumption that the physical risks and operational burdens on the staff could be alleviated by using ultraviolet of a wavelength of not greater than 230 nm, which is generally considered to be less harmful to the human body, for sterilization, in such food-handling sites, the inventor(s) of the present application carried out intensive research to find out if there were any practical issues. As a result, the inventor(s) newly discovered that radiation from a KrCl excimer lamp with a peak wavelength at 222 nm on a human hand or arm produced an odor. More specifically, it was confirmed that an odor that resembled a smell of burning hair arose. It was further confirmed that this odor could not be removed even by washing with soap, after the ultraviolet irradiation.

As described also in Patent Document 1, ultraviolet irradiation of the human body in such a wavelength band in a clinical site hardly raises an issue of such characteristic smell resulting from ultraviolet irradiation, because of the distinct chemical smells present in the clinical site. In a food-handling site or store, however, the presence of such an odor will pose a problem, and this could inhibit introduction of the practice of sterilization with ultraviolet irradiation.

Spraying of a deodorant spray containing alcohol would be a possible method to control this odor in a food-handling site or store, but it is hardly effective since the odor comes back after the alcohol components have evaporated.

In consideration of the problems described above, an object of the present invention is to provide a method of sterilization by ultraviolet irradiation whereby effects on the human body can be mitigated and an odor that arises after ultraviolet irradiation can be controlled. Another object of the present invention is to provide an apparatus suited to realize such a sterilization method.

Means for Solving the Problems

A sterilization method according to the present invention includes:

a step (a) of irradiating a skin of a hand or arm with ultraviolet having a wavelength of 200 nm or more and 230 nm or less; and a step (b) of applying a topical skin preparation, cosmetic, or aqueous solution containing at least one amino acid or amino acid derivative selected from an amino acid group A to a region of the skin irradiated with the ultraviolet, the amino acid group A including valine, leucine, isoleucine, glutamic acid, arginine, serine, aspartic acid, proline, and glycine.

The topical skin preparation, cosmetic, or aqueous solution applied in the step (b) may contain a moisturizing component or an adhesion/permeation component.

The step (a) may be a step of irradiating the skin with radiation light from an excimer lamp containing a gas including KrCl or KrBr for light emission.

The steps (a) and (b) may be performed in a non-clinical site.

A sterilization apparatus according to the present invention is a sterilization apparatus for sterilizing a skin of a hand, wrist, or arm, including:

a light source capable of radiating ultraviolet having a wavelength of 200 nm or more and 230 nm or less;

an insertion hole for allowing an ultraviolet irradiation target region including a hand, wrist, or arm to be inserted from outside the sterilization apparatus into the sterilization apparatus; and a spray port for spraying a topical skin preparation, cosmetic, or aqueous solution containing at least one amino acid or amino acid derivative selected from an amino acid group A, the amino acid group A including valine, leucine, isoleucine, glutamic acid, arginine, serine, aspartic acid, proline, and glycine.

The light source may include an excimer lamp containing a gas including KrCl or KrBr for light emission.

The sterilization apparatus may be configured such that the topical skin preparation, cosmetic, or aqueous solution is sprayed automatically from the spray port after the ultraviolet irradiation target region has been irradiated with the ultraviolet from the light source.

The sterilization apparatus may include a platform arranged inside the insertion hole for adjustment of a spacing distance between the ultraviolet irradiation target region and the light source.

The sterilization apparatus may include a sensor capable of detecting insertion of the ultraviolet irradiation target region into the sterilization apparatus, and the light source may radiate the ultraviolet automatically for a predetermined period of time when the sensor detects insertion of the ultraviolet irradiation target region into the sterilization apparatus.

The sterilization apparatus may be used for non-clinical applications.

Effect of the Invention

The present invention allows for ultraviolet irradiation for the purpose of sterilization while mitigating the effects on the human body and controlling odor generation after the sterilization process.

MODE FOR CARRYING OUT THE INVENTION

The method according to the present invention is composed of the following two steps. The two steps are: step (a) irradiating a skin of a hand or arm with ultraviolet having a wavelength of 200 nm or more and 230 nm or less; and step (b) applying a topical skin preparation, cosmetic, or aqueous solution containing at least one amino acid or amino acid derivative selected from the following amino acid group A to a region of the skin irradiated with the ultraviolet. The "amino acid group A" in the step (b) is a group including valine, leucine, isoleucine, glutamic acid, arginine, serine, aspartic acid, proline, and glycine.

<Step (a): Ultraviolet Irradiation Step>

Ultraviolet irradiation of the skin of a hand or arm with a wavelength of 200 nm or more and 230 nm or less has little effect on the human body. This is because when the human body is irradiated with this wavelength band, the ultraviolet is absorbed in the stratum corneum of the skin and does not propagate deeper than that (toward the stratum basale). Corneocytes in the stratum corneum are cells without a nucleus, and do not contain DNA as with, for example, spinous cells. Therefore, there is hardly any risk of DNA being destroyed by ultraviolet absorbed by the cells, as with when irradiated with ultraviolet with a wavelength of about 250 nm. It is therefore possible to adjust the intensity or time of ultraviolet irradiation depending on the required sterilization performance.

It is preferable to use a shorter wavelength of ultraviolet from the viewpoint of mitigating the effects on the cell nuclei (DNA) of the human body. However, the ultraviolet radiation in the wavelength band of less than 200 nm is absorbed by the air (oxygen in the air) so that the amount of light is largely reduced when the light reaches the skin of a hand or arm. Therefore, no sterilization effects can be guaranteed.

As a light source of ultraviolet having a wavelength of 200 nm or more and 230 nm or less, an excimer lamp containing a gas including KrCl or KrBr for light emission can be used. This light source should preferably include a built-in filter for cutting light rays of wavelengths longer than 230 nm.

Figure 1:
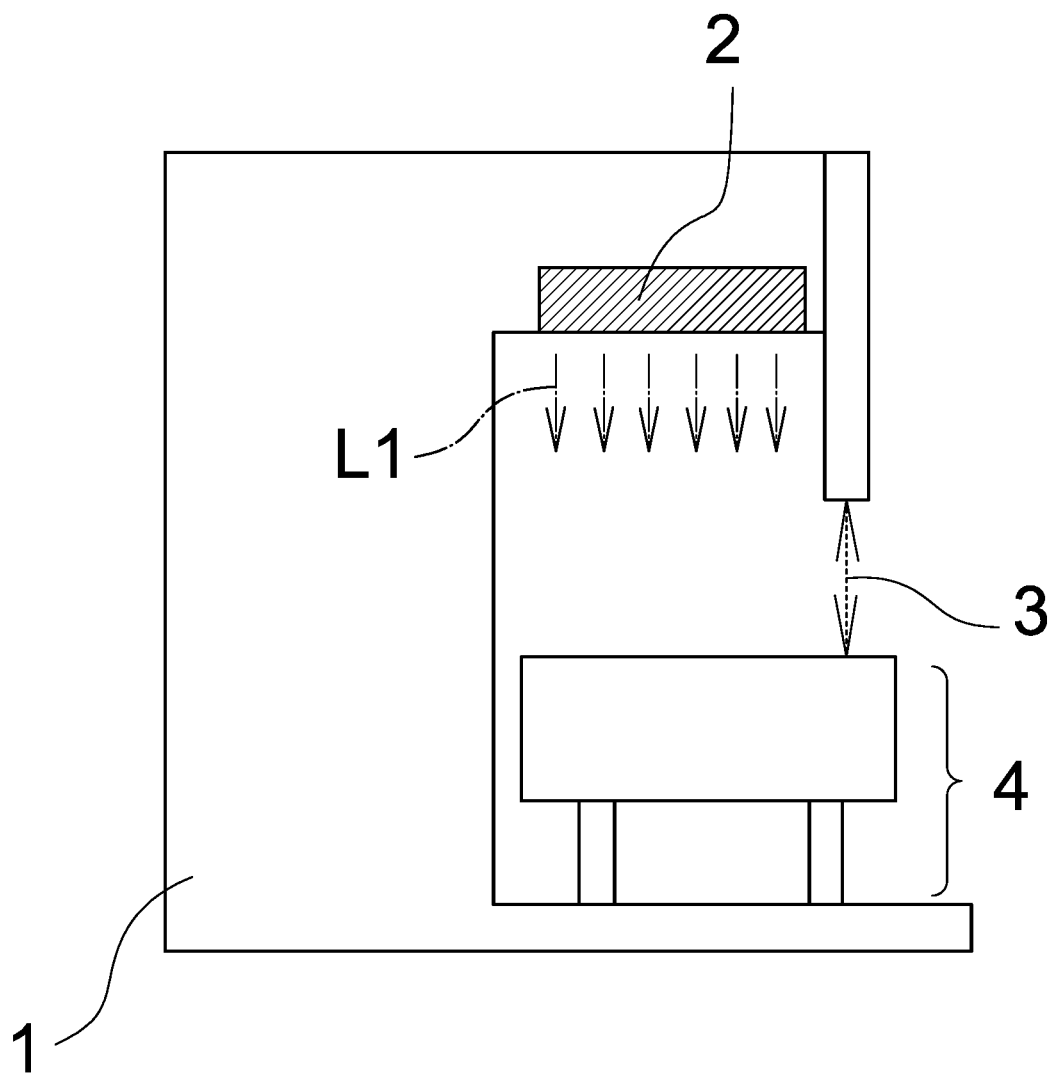
FIG. 1 is a schematic diagram illustrating a configuration of an ultraviolet irradiation apparatus.

For example, an ultraviolet irradiation apparatus 1 shown in FIG. 1 may be utilized. The ultraviolet irradiation apparatus 1 includes a light source 2 capable of radiating ultraviolet having a wavelength of 200 nm or more and 230 nm or less, and an insertion hole 3 for allowing an ultraviolet irradiation target region such as a hand, wrist, or arm to be inserted into the apparatus 1. As required, the apparatus may be equipped with a platform 4 as shown in FIG. 1. The platform 4 is provided for adjustment of the spacing distance between the light source 2 and the irradiation target (such as a wrist or a palm of the hand). When using this ultraviolet irradiation apparatus 1, a hand or wrist is inserted from the insertion hole 3, to irradiate the hand, wrist, or arm with the ultraviolet L1 from the light source 2. The ultraviolet irradiation apparatus 1 may be configured with a predetermined built-in sensor (not shown), so that power is supplied automatically to the light source 2 and ultraviolet L1 is emitted for a predetermined period of time when insertion of a hand or wrist from the insertion hole 3 is detected.

When a hand or arm was irradiated with ultraviolet with a wavelength of 200 nm or more and 230 nm or less, a smell (odor) that resembled that of burning hair arose. This smell could not be removed by a wash with a soap. The details will be described later with reference to test examples.

<Step (b): Amino Acid Application Step>

A topical skin preparation, cosmetic, or aqueous solution containing at least one amino acid or amino acid derivative selected from the amino acid group A is applied to a region irradiated with the ultraviolet in the step (a), the amino acid group A including valine, leucine, isoleucine, glutamic acid, arginine, serine, aspartic acid, proline, and glycine. It was confirmed that the odor mentioned above was removed by this step. Hereinafter, the "topical skin preparation, cosmetic, or aqueous solution containing at least one amino acid or amino acid derivative selected from the amino acid group A" shall be referred to as "specified solvent B".

The inventor(s) of the present application speculated that the odor that arose after the step (a) was performed resulted from destruction of some of the amino acids contained in the keratin (epidermal keratin) in the corneocytes when irradiated with ultraviolet, and originated from a substance different from the amino acids. It is assumed that the destroyed amino acid was repaired by applying the specified solvent B in the region irradiated with ultraviolet so that aldehyde was reduced, as a result of which the odor was removed. The details will be described later with reference to test examples.

As for irradiation of a hand or arm with ultraviolet at a wavelength of about 250 nm, the issue of whether or not there is an odor hardly becomes apparent because of the intrinsically large effects on the human body as described above. Moreover, if a hand or arm were irradiated with about 250 nm wavelength ultraviolet, the amount of light absorbed by the corneocytes would be lower than when irradiated with ultraviolet with a wavelength of 200 nm or more and 230 nm or less, since the light passes through the stratum corneum and reaches the stratum granulosum or stratum spinosum, and sometimes even the stratum basale. Therefore, it is assumed that, the issue of an odor originating from destruction of some of the amino acids contained in the epidermal keratin hardly becomes apparent with ultraviolet irradiation at a wavelength of 250 nm as compared with ultraviolet irradiation at a wavelength of 200 nm or more and 230 nm or less.

The specified solvent B may take any form and may be formulated in the form of any of a liquid, emulsion, gel, spray, foam, and so on. The specified solvent B may be prepared in any way as long as it contains at least one amino acid or amino acid derivative selected from the amino acid group A, and may contain any of other components commonly mixed in pharmaceutical or quasi-pharmaceutical products, cosmetics and the like such as, for example, anionic surfactant, ampholytic surfactant, non-ionic surfactant, thickening agent, oil agent, preservative, perfume, moisturizer, bioactive component, antioxidant, sequestrant, pH adjuster, water, alcohol, colorant, fragrance component, and so on, as required.

From the viewpoint of repair of amino acids contained in the epidermal keratin that were destroyed in the step (a), the specified solvent B should more preferably contain components that provide moisturizing and adhesion/penetration effects. As moisturizing components, for example, sodium hyaluronate, sodium pyrrolidonecarboxylic acid (PCA-Na) aqueous solution, butylene glycol, and glycerin can be applied. As components that provide adhesion/penetration effects, dimethicone and carbomer (carboxy vinyl polymer) can be applied.

Hereinafter, the present invention will be described in detail with reference to test examples.

Test Example 1

Using the ultraviolet irradiation apparatus 1 shown in FIG. 1, the palms of right hands of six assessors M1, M2, M3, M4, M5, and M6 were irradiated with ultraviolet, with a peak wavelength at 222 nm and an irradiance of 3.8 mW/cm$^2$ for an irradiation period of 30 seconds. The palm and the light source were spaced apart by 8 cm. The ultraviolet irradiation apparatus 1 was an apparatus having an excimer lamp containing KrCl gas for light emission as a light source 2. The spacing distance between the UV-irradiated point and the light source was adjusted with the platform 4. The same applies to the following test examples.

Whether there is an odor or not was judged each time (1-1) immediately after the irradiation, (1-2) one minute after the irradiation, and (1-3) after the hand and arm were washed using alkaline soap after one minute after the irradiation. Table 1 shows the judgement results.

TABLE 1

| | (1-1) Immediately after irradiation | (1-2) Several minutes after irradiation | (1-3) After a wash with soap |
|---|---|---|---|
| M1 | Odor detected | Oder detected | Oder detected |
| M2 | Odor detected | Oder detected | Oder detected |
| M3 | Odor detected | Oder detected | Oder detected |
| M4 | Odor detected | Oder detected | Oder detected |
| M5 | Odor detected | Oder detected | Oder detected |
| M6 | Odor detected | Oder detected | Oder detected |

As shown in Table 1, all six assessors determined that there was an odor each time (1-1) immediately after the irradiation, (1-2) one minute after the irradiation, and (1-3) after the hand and arm were washed using alkaline soap after one minute after the irradiation.

Further, after sterilizing the hands and arms of the six assessor M1, M2, M3, M4, M5, and M6 with alcohol prior to the ultraviolet irradiation, their hands and arms near the wrists were irradiated with ultraviolet, similarly to Test Example 1. In this case, too, similarly to Test Example 1, all six assessors determined that there was an odor each time (1-1) immediately after the irradiation, (1-2) one minute after the irradiation, and (1-3) after the hand and arm were washed using alkaline soap after one minute after the irradiation.

Test Example 2

Using the same light source as that of the ultraviolet irradiation apparatus 1, artificial skin produced by Japan Tissue Engineering Co., Ltd was irradiated with ultraviolet with a peak wavelength at 222 nm. The result was that an odor similar to that of Test Example 1 was generated.

Since artificial skin is fabricated in aseptic conditions, it is assumed that the odor originates from a protein rather than a bacteria, based on the results of Test Example 1 and Test Example 2.

Test Example 3

Looking at amino acids that form the proteins in the epidermis, then changes in the odor before and after irradiation of ultraviolet at a peak wavelength of 222 nm with respect to the following eighteen types of amino acids are examined More specifically, a 3 mL aqueous solution of each type of amino acid was put in a φ40 petri dish, and using the same light source as that of the ultraviolet irradiation apparatus 1, irradiated with ultraviolet with an irradiance of 3.8 mW/cm$^2$ for an irradiation period of 30 seconds. The petri dish and the light source were spaced apart by 8 cm. The eighteen types of amino acids were: Cystine, glutamic acid, leucine, arginine, serine, threonine, aspartic acid, proline, glycine, valine, alanine, phenylalanine, isoleucine, tyrosine, lysine, histidine, methionine, and tryptophan. These eighteen amino acids are all known as the substances that form proteins contained in the epidermis.

Table 2 shows the judgement results. Table 2 shows the odor before the ultraviolet irradiation, the odor after the ultraviolet irradiation, and comparison with the odor in Test Example 1 after the ultraviolet irradiation. The comparison with the odor in Test Example 1 was made by sensory evaluation performed by the six assessors M1, M2, M3, M4, M5, and M6.

TABLE 2

| Amino acid name | Before irradiation | After irradiation | Comparison with smells in Test example 1 |
|---|---|---|---|
| Cystine | No smell | No smell (no change) | Different |
| Glutamic acid | Slight smell | Slight smell (no change) | Different |
| Leucine | Characteristic smell | Smell of burning hair | Almost identical |
| Arginine | Characteristic smell | Characteristic smell (no change) | Different |
| Serine | No smell | No smell (no change) | Different |
| Threonine | No smell | No smell (no change) | Different |
| Aspartic acid | No smell | No smell (no change) | Different |
| Proline | No smell | Smell like lysine | Different |
| Glycine | No smell | No smell (no change) | Different |
| Valine | Characteristic smell | Smell of burning hair | Almost identical |
| Alanine | Slight sour smell | Slight sour smell (no change) | Different |
| Phenylalanine | Slightly less sweet smell | Change in type of sweetness | Different |
| Isoleucine | Characteristic smell | Smell of burning hair | Almost identical |
| Tyrosine | No smell | No smell (no change) | Different |
| Lysine | Characteristic smell | Characteristic smell (no change) | Different |
| Histidine | No smell | No smell (no change) | Different |
| Methionine | Smell of slightly rotting onions | Smell of burning hair | Almost identical |

As shown in Table 2, with respect to leucine, valine, isoleucine, and methionine, it was confirmed that each of these amino acids produced an odor that was substantially the same as that detected after the ultraviolet irradiation of a human hand or arm after the irradiation of ultraviolet at a wavelength of 222 nm. It is considered, from these test results, that the odor that arose when the hand or arm was irradiated with 222 nm wavelength ultraviolet resulted from decomposition of one of the amino acids that form the skin, i.e., leucine, valine, isoleucine, and methionine.

Test Example 4

Similarly to the method of Test Example 1, using the ultraviolet irradiation apparatus 1 shown in FIG. 1, the palm of the right hand of each of six assessors M1, M2, M3, M4, M5, and M6 was irradiated with ultraviolet, with a peak wavelength at 222 nm and an irradiance of 3.8 mW/cm$^2$ for an irradiation period of 30 seconds.

After that, each aqueous solution of the eighteen types of amino acids used in Test Example 3 (cystine, glutamic acid, leucine, arginine, serine, threonine, aspartic acid, proline, glycine, valine, alanine, phenylalanine, isoleucine, tyrosine, lysine, histidine, methionine, and tryptophan) was applied to the region irradiated with ultraviolet (molar concentration: 1 mM). More specifically, each aqueous solution was sprayed and rubbed in with the palm of the hand. This was followed by an assessment of any changes in the smell before and after application of each aqueous solution.

Table 3 shows the judgement results. While Table 3 shows only the results given by Assessor M1, the other five assessors gave exactly the same results.

TABLE 3

| Amino acid name | Before application of amino acid solution | After application of amino acid solution |
|---|---|---|
| Cystine | Smell of burning hair | Smell of burning hair (no change) |
| Glutamic acid | | Smell disappeared |
| Leucine | | Smell disappeared |
| Arginine | | Smell disappeared |
| Serine | | Smell disappeared |
| Threonine | | Smell of burning hair (no change) |
| Aspartic acid | | Smell disappeared |
| Proline | | Smell disappeared |
| Glycine | | Smell disappeared |
| Valine | | Smell disappeared |
| Alanine | | Smell of burning hair (no change) |
| Phenylalanine | | Smell of burning hair (no change) |
| Isoleucine | | Smell disappeared |
| Tyrosine | | Smell of burning hair (no change) |
| Lysine | | Smell of burning hair (no change) |
| Histidine | | Smell of burning hair (no change) |
| Methionine | | Smell disappeared |
| Tryptophan | | Smell of burning hair (no change) |

The results in Table 3 show that no odor was detected when an aqueous solution of leucine, valine, isoleucine, or methionine was applied after ultraviolet irradiation, which were assumed to be the source of odor in Test Example 3. The results also show that, apart from leucine, valine, isoleucine, and methionine, no odor was detected when an aqueous solution of glutamic acid, arginine, serine, aspartic acid, proline, or glycine was applied after ultraviolet irradiation.

It is concluded from the results of Test Example 3 and Test Example 4 that irradiation of the skin with ultraviolet at a wavelength of 222 nm destroys some amino acids and produces an odor, but applying a specific amino acid to the UV-irradiated skin thereafter repairs part or all of the destroyed amino acids, whereby the source of the odor is eliminated and the odor disappears.

While the test examples described above were performed using ultraviolet of a wavelength of 222 nm, it is concluded that, with the light of wavelengths around 222 nm, and the light of wavelengths shorter than 222 nm, an odor arises in the step (a), and the odor that arose is reduced in the step (b), by the same principles.

The results of Test Examples 3 and 4 described above confirmed that application of a specific amino acid after irradiation of ultraviolet at a wavelength of 222 nm stopped the odor. It follows that, for the same reasons, odor generation can be controlled by application of a material containing this specific amino acid, or a material containing a derivative of this specific amino acid.

Test Example 5

Similarly to Test Example 4, using the ultraviolet irradiation apparatus 1 shown in FIG. 1, the palm of the right hand of each of six assessors M1, M2, M3, M4, M5, and M6 was irradiated with ultraviolet, with a peak wavelength at 222 nm and an irradiance of 3.8 mW/cm² for an irradiation period of 30 seconds.

After that, the following four commercial products were applied to the region irradiated with ultraviolet.

(Commercial product A) Amino acid penetration gel produced by MATSUYAMA CO., LTD.
Moisturizer contents: Sodium hyaluronic acid, sodium PCA, butylene glycol, and sodium lactate
Amino acid contents: Proline, glycine, arginine, and betaine
Adhesion/penetration contents: Carbomer (carboxy vinyl polymer)

(Commercial product B) Atrix hand gel produced by Nivea-Kao Co., Ltd.
Moisturizer contents: Sodium hyaluronic acid, sodium PCA, butylene glycol, and glycerin
Amino acid contents: Proline, glycine, arginine, betaine, and lauroyl glutamate
Adhesion/penetration contents: Dimethicone and carbomer (carboxy vinyl polymer)

(Commercial product C) Men's deodorant spray produced by Shiseido Company, Limited
Moisturizer contents: None
Amino acid contents: None
Adhesion/penetration contents: None
Other ingredients: Disinfectant (IPMP: Isopropyl Methylphenol), zinc oxide, and deodorant (alum)

(Commercial product D) Sunscreen cream produced by Taisho Pharmaceutical Co., Ltd.
Moisturizer contents: Glycerin and butylene glycol
Amino acid contents: None
Adhesion/penetration contents: Dimethicone
Other ingredients: UV absorber (ethylhexyl methoxycinnamate, diethylamino hydroxybenzoyl hexyl benzoate), oil and grease (for shine, skin protection, etc.)

Table 4 shows the judgement results. While Table 4 shows only the results given by Assessor M1, the other five assessors gave exactly the same results.

TABLE 4

| Applied pharmaceutical formulation | Amino acid content | Before application of pharmaceutical formulation | After application of pharmaceutical formulation |
|---|---|---|---|
| Commercial product A | Contained | Smell of burning hair | Smell disappeared |
| Commercial product B | Contained | | Smell disappeared |
| Commercial product C | Not contained | | Smell of burning hair (no change) |
| Commercial product D | Not contained | | Smell of burning hair (no change) |

The results in Table 4 ascertained that the odor after ultraviolet irradiation was not necessarily removed only by the application of a pharmaceutical formulation designed to provide a function such as adhesion, penetration, and removal of smell. The results in Table 4 also indicate that the speculation obtained based on the test results of Test Examples 1 to 4 is correct. Namely, it confirms that irradiation of the skin with ultraviolet at a wavelength of 222 nm destroys some amino acids and produces an odor, but applying a specific amino acid (proline, glycine, and arginine in Test Example 5) to the UV-irradiated skin thereafter repairs part or all of the destroyed amino acids, whereby the source of the odor is eliminated and the odor disappears.

Other Embodiments

Figure 2:
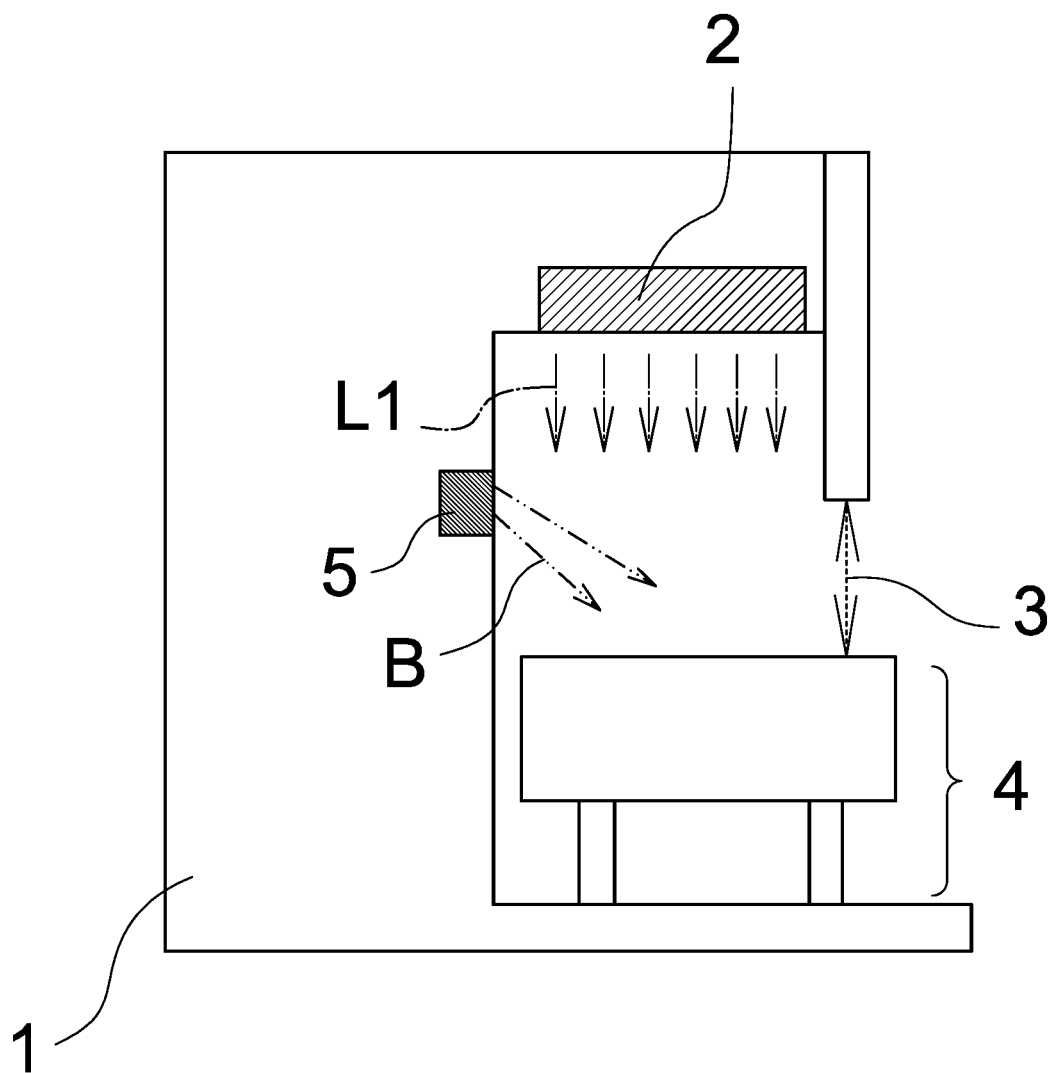
FIG. 2 is a schematic diagram illustrating another configuration of the ultraviolet irradiation apparatus.

As shown in FIG. 2, the ultraviolet irradiation apparatus 1 may be equipped with a spray port 5 for spraying a topical skin preparation, cosmetic, or aqueous solution containing at least one amino acid or amino acid derivative selected from the specified solvent B to a UV-irradiated point, the specified solvent B including valine, leucine, isoleucine, glutamic acid, arginine, serine, aspartic acid, proline, and glycine. Thus a worker's hand or arm, when inserted into the apparatus 1, is automatically irradiated with ultraviolet with a wavelength of 200 nm or more and 230 nm or less for a predetermined period of time, after which a specified solvent B is successively sprayed onto the irradiated region. Therefore, the worker only needs to rub in the specified solvent B with the hands after taking his or her hand or arm out of the apparatus 1, whereby sterilization is achieved while odor generation is controlled.

DESCRIPTION OF REFERENCE SIGNS

1 Ultraviolet irradiation apparatus
2 Light source
3 Insertion hole
4 Platform
5 Spray port
L1 Ultraviolet
B Specified solvent

The invention claimed is:

1. A sterilization method comprising:
    a step (a) of irradiating a skin of a hand or arm with ultraviolet having a wavelength of 200 nm or more and 230 nm or less; and
    a step (b) of applying a topical skin preparation, cosmetic, or aqueous solution containing at least one amino acid or amino acid derivative selected from an amino acid group A to a region of the skin irradiated with the ultraviolet,
    the amino acid group A including valine, leucine, isoleucine, glutamic acid, arginine, serine, aspartic acid, proline, and glycine.

2. The sterilization method according to claim 1, wherein the topical skin preparation, cosmetic, or aqueous solution applied in the step (b) contains a moisturizing component or an adhesion/penetration component.

3. The sterilization method according to claim 1, wherein the step (a) is a step of irradiating the skin with radiation light from an excimer lamp containing a gas including KrCl or KrBr for light emission.

4. The sterilization method according to claim 1, wherein the steps (a) and (b) are performed in a non-clinical site.

* * * * *